(12) United States Patent
Faria

(10) Patent No.: US 10,514,079 B2
(45) Date of Patent: Dec. 24, 2019

(54) DECOUPLER

(71) Applicant: Schaeffler Technologies AG & Co. KG, Herzogenaurach (DE)

(72) Inventor: Christof Faria, Erlangen (DE)

(73) Assignee: Schaeffler Technologies AG & Co. KG, Herzogenaurach (DE)

( * ) Notice: Subject to any disclaimer, the term of this patent is extended or adjusted under 35 U.S.C. 154(b) by 0 days.

(21) Appl. No.: 15/545,492

(22) PCT Filed: Feb. 3, 2016

(86) PCT No.: PCT/DE2016/200068
§ 371 (c)(1),
(2) Date: Jul. 21, 2017

(87) PCT Pub. No.: WO2016/124195
PCT Pub. Date: Aug. 11, 2016

(65) Prior Publication Data
US 2018/0283489 A1   Oct. 4, 2018

(30) Foreign Application Priority Data
Feb. 5, 2015 (DE) .......................... 10 2015 202 043

(51) Int. Cl.
*F16F 15/121* (2006.01)
*F16D 3/12* (2006.01)
(Continued)

(52) U.S. Cl.
CPC ............ *F16F 15/1216* (2013.01); *F16D 3/12* (2013.01); *F16D 41/206* (2013.01); *F16D 2300/22* (2013.01); *F16H 7/02* (2013.01)

(58) Field of Classification Search
CPC ... F16D 41/206; F16D 7/022; E05Y 2201/49; E05Y 2800/22; F16H 55/36
(Continued)

(56) References Cited

U.S. PATENT DOCUMENTS 2,885,896 A * 5/1959 Hungerford, Jr. ........ F16H 9/04
192/12 BA
3,019,871 A * 2/1962 Sauzedde ................ F16D 41/00
192/30 V (Continued)

FOREIGN PATENT DOCUMENTS

| CN | 200982361 Y | 11/2007 |
|---|---|---|
| CN | 106687706 A | 5/2017 |

(Continued)

OTHER PUBLICATIONS

Chinese Office Action for CN107208701, 8 pgs; dated Aug. 5, 2019 by the Chinese Patent Office.

*Primary Examiner* — Henry Y Liu
(74) *Attorney, Agent, or Firm* — Matthew V. Evans

(57) ABSTRACT

A decoupler is disclosed for transmitting a drive torque from a rotary drive to a rotary output. The decoupler may include a first spring collar arranged on a drive-part side of a first end of a coil torsion spring and a second spring collar arranged on an output-part side of a second end of the coil torsion spring. The spring collars include axially ascending ramps, and the ends of the coil torsion spring resting thereon widen the coil torsion spring radially with transmission of a drive torque. The ends of the coil torsion spring and the spring collars include reciprocal rotary stops that prevent a relative rotation of the second spring collar with respect to the second coil torsion spring end and of the first coil torsion spring end with respect to the first spring collar.

14 Claims, 3 Drawing Sheets

(51) Int. Cl.
*F16D 3/72* (2006.01)
*F16H 55/36* (2006.01)
*F16D 41/20* (2006.01)
*F16H 7/02* (2006.01)

(58) Field of Classification Search
USPC .......................................................... 474/70
See application file for complete search history.

(56) References Cited

U.S. PATENT DOCUMENTS

| | | | | |
|---|---|---|---|---|
| 5,370,585 A | * | 12/1994 | Thomey | F16H 7/1218 474/112 |
| 6,083,130 A | * | 7/2000 | Mevissen | F02B 67/06 474/70 |
| 7,591,357 B2 | * | 9/2009 | Antchak | F16D 41/206 192/41 S |
| 7,618,337 B2 | * | 11/2009 | Jansen | F02B 67/06 192/41 S |
| 7,975,821 B2 | * | 7/2011 | Antchak | F16D 7/022 192/55.1 |
| 8,047,920 B2 | * | 11/2011 | Jansen | F16D 3/52 464/60 |
| 2010/0178990 A1 | * | 7/2010 | Jansen | F16D 3/52 464/39 |
| 2013/0062155 A1 | * | 3/2013 | Varin | F16F 15/1213 192/41 S |
| 2013/0092501 A1 | * | 4/2013 | Schneider | F16D 41/206 192/41 S |

FOREIGN PATENT DOCUMENTS

| | | |
|---|---|---|
| WO | 199850709 A1 | 11/1998 |
| WO | 2006081657 A1 | 8/2006 |
| WO | 2013124009 A1 | 8/2013 |

* cited by examiner

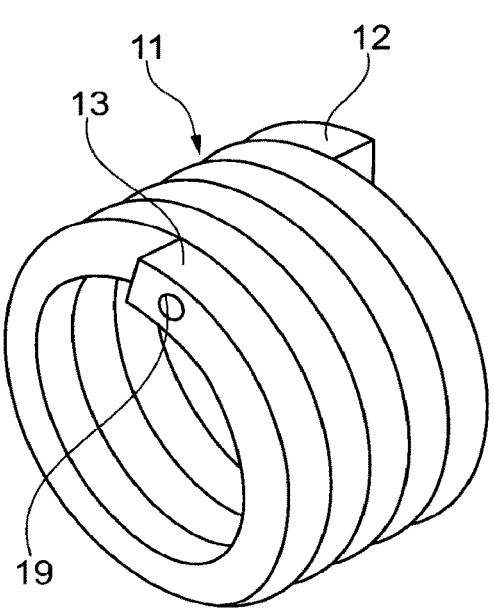
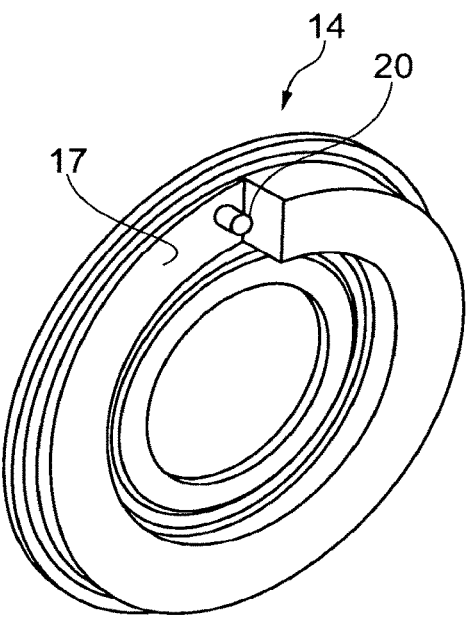
Fig. 9    Fig. 10
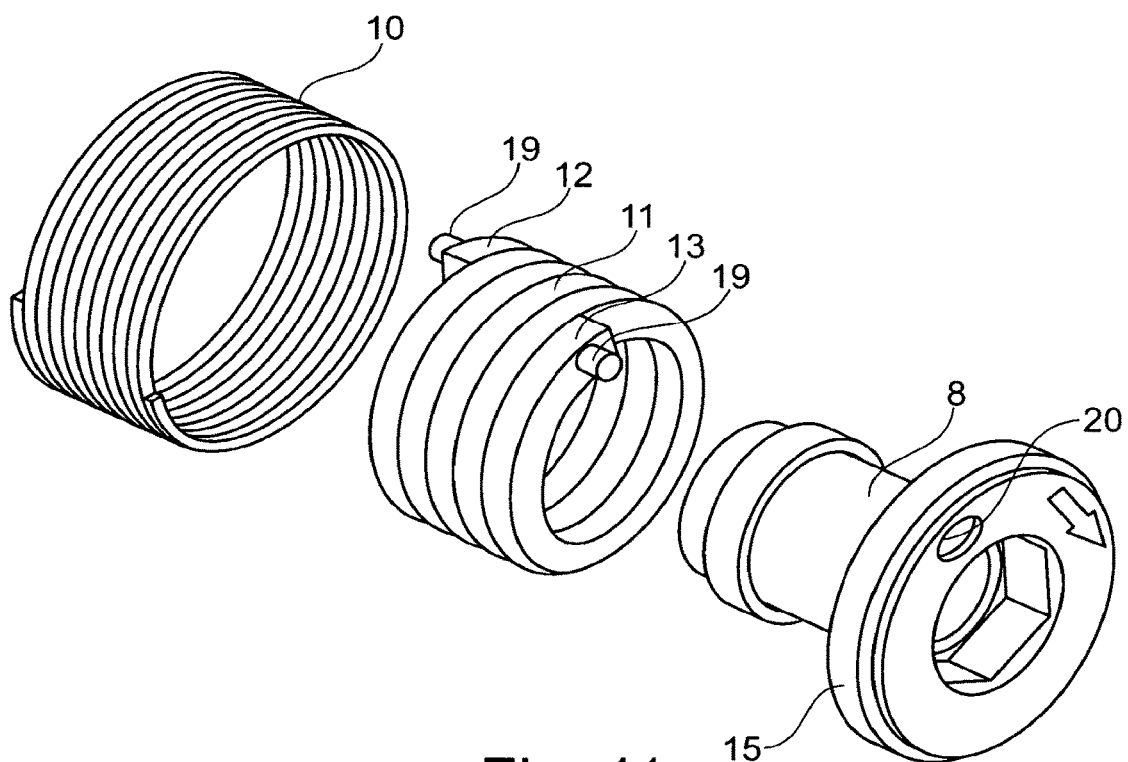
Fig. 11

DECOUPLER

CROSS-REFERENCE TO RELATED APPLICATIONS

This application is the U.S. National Phase of PCT Appln. No. PCT/DE2016/200068 filed Feb. 3, 2016, which claims priority to DE102015202043.6 filed Feb. 5, 2015, the entire disclosures of which are incorporated by reference herein.

TECHNICAL FIELD

The disclosure relates to a decoupler for transmitting a drive torque from a rotary drive to a rotary output.

BACKGROUND

Such decouplers are typically configured as belt pulley decouplers of a belt drive of an auxiliary unit of an internal combustion engine. These decouplers can be arranged as crankshaft decouplers on the crankshaft or as generator decouplers on the generator and compensate the input of torsional vibrations and cyclic irregularities of the crankshaft into the belt drive of the auxiliary unit or into the generator, as the case may be. In the engaged state of the one-way clutch, the series connection which is made up of the one-way clutch and the coil torsion spring transmits the drive torque from the drive part to the output part, and the elasticity of the coil torsion spring smooths the cyclic irregularities. When the rotation of the drive part is retarded, the one-way clutch is disengaged, so that, in reverse, no considerable torque can be transmitted from the output part to the drive part. In the case of the generator decoupler, the generator shaft, which possesses a relatively high mass inertia, can overrun the belt pulley of the generator.

A generic type of generator decoupler is disclosed for example in U.S. Pat. No. 8,047,920 B2. A one-way clutch is configured as a wrap-around band which is situated in the series connection on the drive side and radially between the coil torsion spring and the belt pulley. Although the wrap-around band is disengaged when the generator shaft is in the overrunning state, the frictional torque between the inner peripheral surface of the belt pulley and the wrap-around band clinging thereto can lead to a relative twisting of the two spring collars, so that the ends of the coil torsion springs move away from the peripheral contact sections of the ramp-like spring collars and move upwards along their ramps. Because, due to the ramp geometry, the available axial design space for the coil torsion spring gets effectively reduced during this upward motion, it is possible for the coil torsion spring to press the two spring collars axially apart from each other and thus cause, as it were, a bursting of the belt pulley coupler in the axial direction. An equally undesired consequence is the conspicuous noise generated by the decoupler when one or both of the spring ends run repeatedly upwards along the ramps and snap back against the stops after each revolution.

As a solution to this problem U.S. Pat. No. 8,047,920 B2 proposes a mechanism that blocks the undesired relative twisting of the two spring collars. According to this solution, during overrunning operation, the two spring collars rotate synchronously and as a unit with the coil torsion spring to thus prevent the upward movement of the spring ends along the ramps. The blocking action is realized through a construction having rotary stops which are fixed on the one hand to the output part and on the other hand on the drive-side spring collar and entrain this spring collar during overrunning operation.

SUMMARY

Based on this, the object of the disclosure is to propose a decoupler of the initially mentioned type with an alternative construction that likewise prevents the upward movement of the coil torsion spring along the ramps.

The disclosure achieves the above object through the features described herein. According to these features, the ends of the coil torsion spring and the spring collars comprise reciprocal rotary stops which prevent respectively in the rotational drive direction, a relative twisting of the second spring collar relative to the second end of the coil torsion spring and of the first end of the coil torsion spring relative to the first spring collar.

The disclosure is based on the principle that the coil torsion spring itself couples the two spring collars to each other in rotation in order to prevent the undesired upward movement of the spring ends along the ramps. This is achieved structurally by the fact that the coil torsion spring can be subjected to load not only in the direction in which it transmits the drive torque with a radial widening of the coil spool. Rather, the coil torsion spring can be adequately subjected to load even in the reverse torque direction in which the coil torsion spring contracts in the radial direction. It is only the combination of the adequately high load bearing capacity of the spring in both torque directions that forces the coil torsion spring and both spring collars to rotate as one unit in the overrunning operation of the decoupler so that the undesired overrunning of the second spring collar relative to the first spring collar that causes the undesired upward movement is prevented.

Depending on the positioning of the coil torsion spring within the series connection with the one-way clutch, the following states can occur during the overrunning operation of the decoupler:

When the coil torsion spring is positioned on the output side, i.e., behind the one-way clutch in the torque flow direction, the second spring collar rotating with the overrunning rotary output entrains the second end of the coil torsion spring in opposition to the friction of the disengaged one-way clutch. As a result, during the overrunning operation of the decoupler, the two spring collars and the coil torsion spring run as one unit without the undesired upward movement along the ramps.

When the coil torsion spring is positioned on the drive side, i.e., before the one-way clutch in the torque flow direction, the output-side second spring collar comes to abut against the second end of the coil torsion spring and the first end of the coil torsion spring comes to abut against the first spring collar. The unit formed by the spring collars and the coil torsion spring runs with the overrun rotary drive in opposition to the friction of the disengaged one-way clutch as one unit without the undesired upward movement along the ramps.

The possibility of loading the coil torsion spring in both directions of torque is obtained preferably through rotary stops that are respectively disengageable from each other and thus also can be easily mounted on each other. As an alternative to positively engaging and disengageable connections, the rotary stops may also be fixed respectively in a disengageable manner on each other. In this case, for example, a respective spring end and a respective spring collar are fixed to each other through a press connection or by welding that makes it possible to apply a torque load to the coil torsion spring that leads to a radial contraction of the coil spool. The two rotary stops of the coil torsion spring are preferably symmetric to each other, so that a directional orientation is not required for the mounting of the decoupler.

The directional inversion between the torque load for a radial widening and a radial contraction of the coil spool of the spring can be realized with a slight transition clearance or also without clearance with respect to the mutually engaging and/or disengaging rotary stops.

BRIEF DESCRIPTION OF THE DRAWINGS

Further features of the disclosure will become obvious from the following description and the attached drawings in which the disclosure is elucidated in principle and with reference to examples of embodiment. If not otherwise stated, identical and functionally identical features or components are identified at identical reference numerals. The figures show:

FIG. 9 is the coil torsion spring of a third example of an embodiment, in a perspective view;

FIG. 10 is a spring collar associated to the coil torsion spring of the third example of an embodiment, in a perspective view; and FIG. 11 is the coil torsion spring of a fourth example of an embodiment together with a one-way clutch and an associated output part with integrated spring collar, in a perspective exploded view.

DETAILED DESCRIPTION

Figure 1:
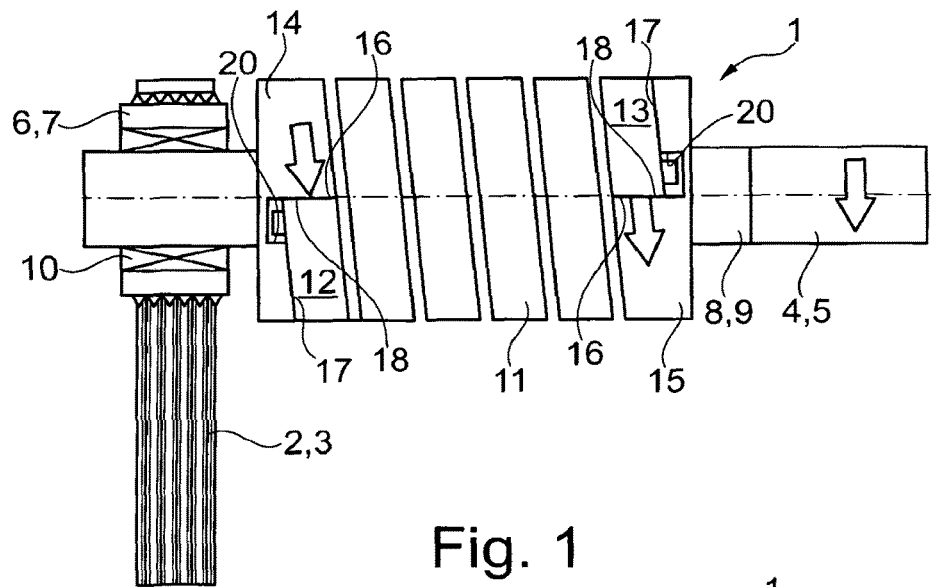
FIG. 1 is an elementary representation of a generator decoupler according to the disclosure, for an auxiliary unit belt drive of an internal combustion engine.

FIG. 1 shows an elementary representation of a decoupler 1 arranged on the generator of an auxiliary unit belt drive of an internal combustion engine. The decoupler 1 transmits the drive torque of the belt 2 as rotary drive 3 to the generator shaft 4 as rotary output 5 and comprises the following components in the drive torque flow:
  a belt pulley 6 surrounded by the belt 2 and arranged as a drive-side drive part 7,
  a hub 8 fixed on the generator shaft 4 and arranged as an output-side output part 9,
  a series connection arranged between the belt pulley 6 and the hub 8 and made up of a one-way clutch 10 and a coil torsion spring 11 whose first end 12 extends on the belt pulley-side and whose second end 13 extends on the hub-side,
  a first spring collar 14 for the first end 12 of the coil torsion spring and
  a second spring collar 15 for the second end 13 of the coil torsion spring.

The drive of the generator takes place in the direction of rotation shown graphically on the generator shaft 4 i.e., in the clockwise direction when the belt drive is viewed in the figure from the left.

The coil torsion spring 11 serving to elastically transmit the drive torque from the belt pulley 6 to the generator shaft 4 is clamped both in the peripheral direction and also slightly biased in the axial direction between the first, drive-side spring collar 14 and the second, output-side spring collar 15. The first spring collar 14 is rotatable both with respect to the belt pulley 6 as well as with respect to the hub 8, and is non-rotatably connected only through the engaged one-way clutch 10 to the belt pulley 6. The second spring collar 15 is fixed in rotation to the hub 8. Both spring collars 14, 15 ascend axially in the manner of ramps (with the respective periphery of their front faces) and are therefore shaped substantially complementarily to the ends 12, 13 of the coil torsion spring 11 that are in contact respectively with the spring collars 14, 15. The transmission of the drive torque is accomplished at both ends 12 and 13 of the coil torsion spring 11 through a respective pressure contact between the front faces 16 of the ends 12, 13 of the coil torsion spring 11 and a respective step 18 formed by the axial ramp 17 of each spring collar 14, 15 so that the coil spool of the coil torsion spring 11 gets radially widened under the drive torque load applied to its ends 12, 13.

The arrows shown on the spring collars 14, 15 in FIG. 1 symbolize the drive torque flow in the decoupler 1 when the hub 8 is being driven in the drive torque direction by the belt pulley 6 in the engaged state of the one-way clutch 10. During this time, the drive torque is transmitted on the one side by the step 18 of the first spring collar 14 to the front face 16 of the first end 12 of the coil torsion spring 11 and, on the other side, by the front face 16 of the second end 13 of the coil torsion spring 11 to the step 18 of the second spring collar 15.

Figure 2:
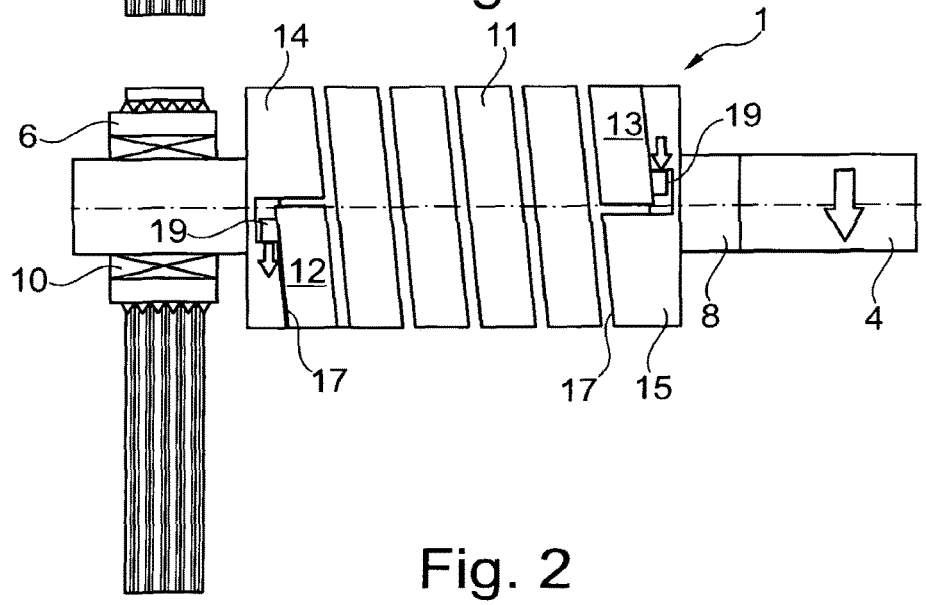
FIG. 2 is the torque flow of the generator decoupler of FIG. 1, in overrunning operation.

FIG. 2 shows the other operational state of the decoupler 1 in which the (inert) generator shaft 4 overruns the belt pulley 6 in the direction of rotation indicated on the shaft 4. An impermissible upward movement of one or both of the ends 12, 13 of the coil torsion spring 11 along the ramps 17 of the spring collars 14, 15 is prevented by respective reciprocal rotary stops 19, 20 provided on both ends 12, 13 of the coil torsion spring 11 and on both spring collars 14, 15 respectively. The rotary stops 19 arranged on the coil torsion spring 11 are formed, each one, as an axial projection on the respective end 12, 13 of the coil torsion spring 11, and the rotary stops 20 arranged on the spring collars 14, 15 are formed, each one, as an axial recess (see FIG. 1) into which the respective projections extend.

Analogous to FIG. 1, the arrows entered in FIG. 2 symbolize the drive torque flow in the decoupler 1 when the belt pulley 6 is overrun by the hub 8 in the drive torque direction in the disengaged state of the one-way clutch 10. During this time, a torque entraining the coil torsion spring 11 is transmitted on the one side by the rotary stop 20 of the second spring collar 15 to the rotary stop 19 of the second end 13 of the coil torsion spring 11 and, on the other side, by the rotary stop 19 of the first end 12 of the coil torsion spring 11 to the rotary stop 20 of the first spring collar 14.

The flow of this entraining torque, whose magnitude depends on the contact friction of the disengaged one-way clutch 10 with the contact partner thereof, enforces a joint rotation of the two spring collar 14, 15 with the coil torsion spring 11 which, itself, transmits the entraining torque. Because even in this case, the spring collars 14, 15 can be twisted relative to each other only within the range of the rotary elasticity of the coil torsion spring 11, the undesired upward movement of the ends 12, 13 of the coil torsion spring 11 along the ramps 17 is always prevented.

Figure 3:
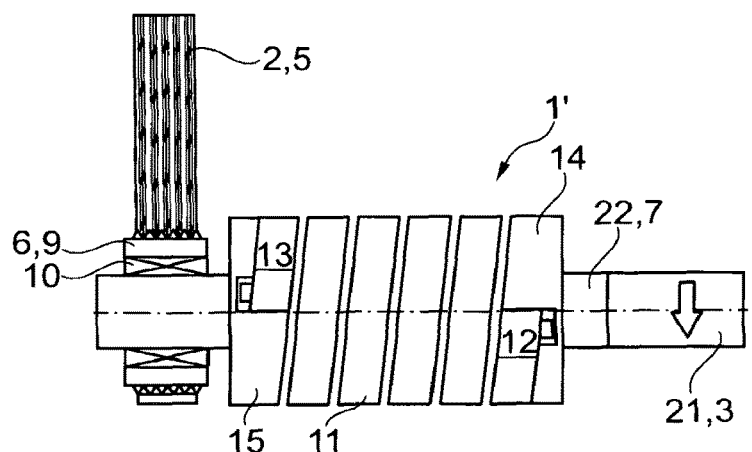
FIG. 3 is an elementary representation of a crankshaft decoupler according to the disclosure for an auxiliary unit belt drive of an internal combustion engine.

FIG. 3 shows an elementary representation of a decoupler 1' that drives the auxiliary unit belt drive of an internal combustion engine. In this case, the crankshaft 21 is the rotary drive 3 and the belt 2 is the rotary output 5. The decoupler 1' comprises following components in the drive torque flow:

a shaft 22 fixed on the crankshaft 21 and arranged as a drive-side drive part 7, a belt pulley 6 surrounded by the belt 2 and arranged as an output-side output part 9, a series connection arranged between the shaft 22 and the belt pulley 6 and made up of a coil torsion spring 11 and a one-way clutch 10, the first end 12 of the coil torsion spring 11 extending on the side shaft-side and the second end 13 of the coil torsion spring 11 extending on the belt pulley-side, a first spring collar 14 for the first end 12 of the coil torsion spring 11 and a second spring collar 15 for the second end 13 of the coil torsion spring 11.

The drive of the belt takes place in the direction of rotation shown graphically on the crankshaft 21 i.e., likewise in the clockwise direction when the belt drive is viewed in the figure from the left. Because, in contrast to FIG. 1, the rotary drive and the rotary output have been exchanged from the left to the right, the winding of the coil torsion spring 11 is also applied in an inversed direction to FIG. 1. With respect to the inventive method of preventing the upward movement along the ramps accomplished with help of the rotary stops 19, 20, however, the above elucidations of FIGS. 1 and 2 apply in an analogical manner.

In FIGS. 1 to 3 the seriation of the one-way clutch 10 and the coil torsion spring 11 that form the series connection can also be exchanged with respect to the drive torque flow. In this case, during overrunning operation, the respective units formed out of the spring collars 14, 15 and the coil torsion spring 11 would rotate synchronously with the belt pulley 6. In addition, the peripheral clearance of the ends 12, 13 of the coil torsion spring 11 at the rotary stops 19, 20 shown in the figures may also be eliminated.

Figure 4:
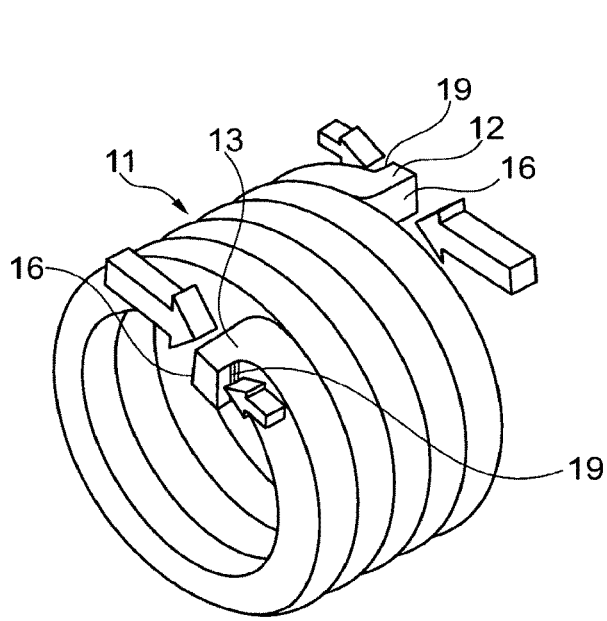
FIG. 4 is the coil torsion spring of a first example of an embodiment, in a perspective view.
Figure 5:
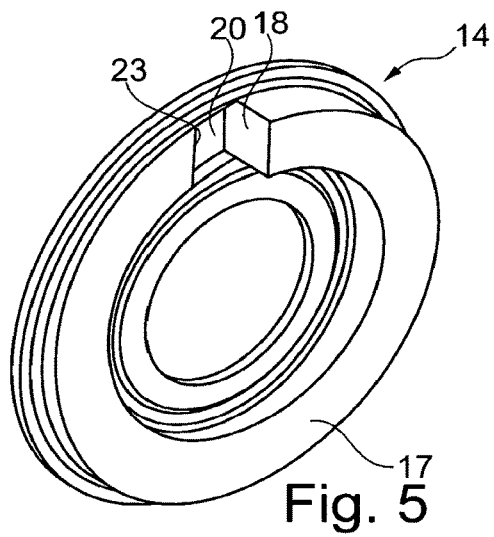
FIG. 5 is a spring collar associated to the coil torsion spring of the first example of an embodiment, in a perspective view.

The coil torsion spring 11 shown in FIG. 4 and a spring collar 14 according to FIG. 5 show a first example of embodiment of rotary stops 19, 20 provided by the disclosure. Both ends 12, 13 of the coil torsion spring 11 made out of a spring wire with rectangular cross-section are bent axially outwards at an angle. The spring collar 14 comprises, in the region of the step 18 formed by the axial ramp 17, an axial recess as a rotary stop 20 into which the angularly bent section of the end 12 of the coil torsion spring 11 projects and abuts against the peripheral border 23 of the recess 20.

The pairs of arrows shown in FIG. 4 symbolize the torque input into the ends 12, 13 of the coil torsion spring 11. The arrows applied to the front faces 16 indicate the drive torque that is then elastically transmitted from the rotary drive to the rotary output by the radially widening coil torsion spring 11. The small arrows symbolize the action on the rear sides of the front faces 16 that serve as spring-side rotary stops 19 and identify the entraining torque that is transmitted from the output-side second spring collar 15 to the drive-side first spring collar 14 by radially contracting coil torsion spring 11.

Figure 6:
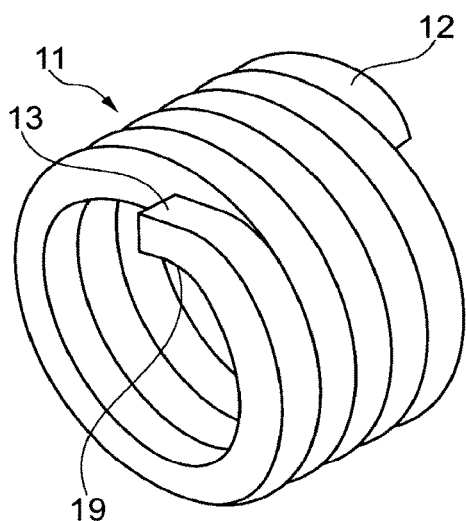
FIG. 6 is the coil torsion spring of a second example of an embodiment, in a perspective view.
Figure 7:
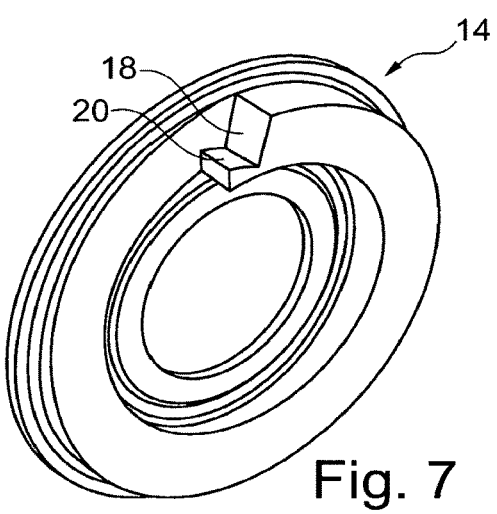
FIG. 7 is a spring collar associated to the coil torsion spring of the second example of an embodiment, in a perspective view.

The coil torsion spring 11 shown in FIG. 6 forms together with the spring collar 14 of FIG. 7 a second example of embodiment of the disclosure. In this case, the spring-side rotary stops 19 are formed by the radially inner sides of the ends 12, 13 of the coil torsion spring 11 that are angled radially inwards and run out somewhat in the manner of a secant with respect to the cylindrical coil spool of the coil torsion spring 11. The associated spring collar-side rotary stop 20 is formed by an inner shoulder that projects from the respective step 18 in the peripheral direction of the spring and is inclined generally complementarily to the end 12 of the coil torsion spring 11 to engage behind the end 12 radially inside. This rear-side engagement enables the application of the entraining torque that effects the radial contraction of the coil torsion spring 11.

Figure 8:
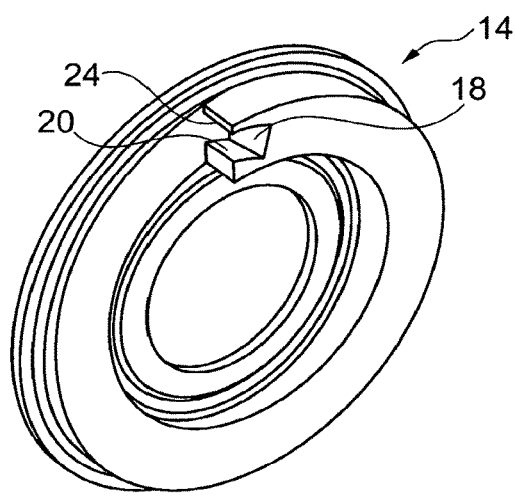
FIG. 8 is an alternative spring collar associated to the coil torsion spring of the second example of an embodiment, in a perspective view.

The spring collar 14 shown in FIG. 8 is a variation of the spring collar 14 shown in FIG. 7. In this embodiment, the inner shoulder 20 as also an outer shoulder 24 project from the step 18 in the peripheral direction of the spring. The outer shoulder 24 extends generally equidistant, with the spring wire thickness, with respect to the inner shoulder 20 and prevents a radially outward deflection of the coil torsion spring end 12 clamped between the two shoulders 20, 24 when the tension force generating the entraining torque is applied to this end 12.

In the third example of embodiment according to FIGS. 9 and 10, the inventive rotary stops 19, 20 are formed on the coil torsion spring 11 by axial recesses in the ends 12, 13 of the coil torsion spring 11 and on the spring collar-sides 14, 15 by axial projections that rise from the ramps 17 and engage into the recesses 19.

FIG. 11 shows a fourth example of embodiment in which the arrangement of the rotary stops 19, 20 has been exchanged and corresponds to that of FIGS. 1 to 3. The rotary stops 19, 20 are formed on the coil torsion spring 11 by axial projections on the ends 12, 13 of the coil torsion spring 11 and on the spring collar-sides 14, 15 by axial recesses in the ramps 17 into which the projections 19 engage. The exploded representation shows on the left of the coil torsion spring 11 the one-way clutch 10 and on the right of the coil torsion spring 11 the hub 8 of the generator decoupler 1. The one-way clutch 10 is a wrap-around band positioned on the drive-side, and hub 8 to be screwed onto the generator shaft 4 is an integral part of the (output-side) second spring collar 15.

As an alternative to the shown rotary stops 19, 20 of the ends 12, 13 of the coil torsion spring 11 and the spring collars 14, 15, a variety of further configurations may be used as long as the rotary stops can apply the entraining torque responsible for the radial contraction of the coil torsion spring to the ends of the coil torsion spring. Such alternatives can be, for example:

non circular projections and/or recesses;
radially oriented projections and recesses;
radially outward angled coil torsion spring ends; and/or
radial or axial bent regions of the coil torsion spring ends with an angle of >90° and <180°.

LIST OF REFERENCE CHARACTERS

1 Decoupler
2 Belt
3 Rotary drive
4 Generator shaft

5 Rotary output
6 Belt pulley
7 Drive part
8 Hub
9 Output part
10 One-way clutch
11 Coil torsion spring
12 First end of coil torsion spring
13 Second end of coil torsion spring
14 First spring collar
15 Second spring collar
16 Front face of a coil torsion spring end
17 Ramp of a spring collar
18 Step
19 Rotary stop of a coil torsion spring end
20 Rotary stop of a spring collar
21 Crankshaft
22 Shaft
23 Limitation of the axial recess of a spring collar
24 Outer shoulder of a spring collar

The invention claimed is:

1. A decoupler for transmitting a drive torque from a rotary drive to a rotary output, said decoupler comprising:
a drive part arranged in a drive torque flow on a drive-side;
an output part arranged in the drive torque flow on an output-side;
a series connection situated between the drive part and the output part and made up of a coil torsion spring and a one-way clutch which permits overrunning of the output part with respect to the drive part in a rotational drive direction;
a first spring collar arranged in the drive torque flow on the drive-side for a first end of the coil torsion spring;
a second spring collar arranged in the drive torque flow on the output-side for a second end of the coil torsion spring;
the first and second spring collars including axially ascending ramps, and the ends of the coil torsion spring resting thereon widening the coil torsion spring radially with transmission of the drive torque; and
the coil torsion spring ends and the spring collars including reciprocal rotary stops that in the rotational drive direction, respectively prevent a relative rotation of the second spring collar with respect to the second end of the coil torsion spring and of the first end of the coil torsion spring with respect to the first spring collar; and,
in a disengaged state of the one-way clutch, a torque entraining the coil torsion spring is transmitted on the output-side from the rotary stop of the second spring collar to the rotary stop of the second end of the coil torsion spring, and on the drive-side from the rotary stop of the first end of the coil torsion spring to the rotary stop of the first spring collar.

2. The decoupler of claim 1, wherein the decoupler drives a generator of an auxiliary unit belt drive of an internal combustion engine, wherein:
the rotary drive is the belt of the belt drive,
the drive part is a belt pulley,
the rotary output is a generator shaft; and
the output part is a hub to be fixed on the generator shaft.

3. The decoupler of claim 1, wherein the rotary stops are formed on the coil torsion spring by axially outward angled coil torsion spring ends and, on the spring collar, by peripheral limitations of axial recesses into which the coil torsion spring ends protrude.

4. The decoupler of claim 1, wherein the rotary stops are formed on the coil torsion spring by radially inward angled coil torsion spring ends and on the spring collar by inner shoulders that engage behind the coil torsion spring ends radially on the inside.

5. The decoupler of claim 4, wherein the coil torsion spring ends are supported radially on the outside against outer shoulders of the spring collars.

6. The decoupler of claim 5, wherein the outer shoulders extend equidistant to the inner shoulders.

7. The decoupler of claim 1, wherein the rotary stops are formed on the coil torsion spring by axial recesses in the coil torsion spring ends and on the spring collar by axial projections that project into the recesses.

8. The decoupler of claim 1, wherein the rotary stops are formed on the coil torsion spring by axial projections on the coil torsion spring ends and on the spring collar by axial recesses into which the projections extend.

9. The decoupler of claim 2, wherein the second spring collar is fixed in rotation to the hub.

10. The decoupler of claim 2, wherein the first spring collar is non-rotatably connected to the belt pulley in an engaged state of the one-way clutch.

11. The decoupler of claim 1, wherein (i) the second end of the coil torsion spring is fixed to the second spring collar by a press-fit connection or a welded connection; or (ii) the first end of the coil torsion spring is fixed to the first spring collar by a press-fit connection or a welded connection.

12. The decoupler of claim 1, wherein the rotary stop of the first end of the coil torsion spring is symmetric to the rotary stop of the second end of the coil torsion spring.

13. The decoupler of claim 1, wherein the decoupler drives an auxiliary unit belt drive of an internal combustion engine, wherein:
the rotary drive is crankshaft,
the drive part is a shaft connected to the crankshaft,
the rotary output is the belt of the belt drive; and
the output part is a belt pulley.

14. A decoupler for transmitting a drive torque from a rotary drive to a rotary output, said decoupler comprising:
a drive part arranged in a drive torque flow on a drive-side;
an output part arranged in the drive torque flow on an output-side;
a series connection situated between the drive part and the output part and made up of a coil torsion spring and a one-way clutch which permits overrunning of the output part with respect to the drive part in a rotational drive direction;
a first spring collar arranged in the drive torque flow on the drive-side for a first end of the coil torsion spring;
a second spring collar arranged in the drive torque flow on the output-side for a second end of the coil torsion spring;
the first and second spring collars including axially ascending ramps, and the ends of the coil torsion spring resting thereon widening the coil torsion spring radially with transmission of the drive torque; and
the coil torsion spring ends and the spring collars including reciprocal rotary stops that in the rotational drive direction, respectively prevent a relative rotation of the second spring collar with respect to the second end of the coil torsion spring and of the first end of the coil torsion spring with respect to the first spring collar; and,
in an engaged state of the one-way clutch, the drive torque is transmitted: (i) from the drive part to the coil torsion spring by a step of the first spring collar to a front face of the first end of the coil torsion spring, and, (ii) from the coil torsion spring to the output part by a front face of the second end of the coil torsion spring to a step of the second spring collar.

* * * * *